United States Patent
Voll et al.

(10) Patent No.: US 8,511,184 B2
(45) Date of Patent: Aug. 20, 2013

(54) DEVICE FOR TAKING SAMPLES FROM THE BOTTOM BOUNDARY LAYER OF A WATER BODY

(75) Inventors: Martin Voll, Tallinn (EE); Ants Erm, Tallinn (EE); Andres Voll, Tallinn (EE); Mehis Voll, Tallinn (EE)

(73) Assignee: OÜ Dimentio, Tallinn (EE)

( * ) Notice: Subject to any disclaimer, the term of this patent is extended or adjusted under 35 U.S.C. 154(b) by 208 days.

(21) Appl. No.: 12/877,650

(22) Filed: Sep. 8, 2010

(65) Prior Publication Data

US 2011/0083520 A1    Apr. 14, 2011

(30) Foreign Application Priority Data

Sep. 9, 2009 (EE) .................................. 200900068

(51) Int. Cl.
    *G01N 1/04*     (2006.01)
(52) U.S. Cl.
    USPC .................. 73/864.44; 73/863.81; 73/863.86; 73/864.63
(58) Field of Classification Search
    USPC ............... 73/170.32, 863.51, 863.56, 863.86, 73/864.31, 864.33, 864.44, 864.45, 864.63, 73/864.65, 864.86
See application file for complete search history.

(56) References Cited

U.S. PATENT DOCUMENTS

| | | | | |
|---|---|---|---|---|
| 3,280,633 A * | 10/1966 | Langguth | ................. | 73/864.31 |
| 3,345,879 A * | 10/1967 | Nasu et al. | ................. | 175/403 |
| 3,372,760 A * | 3/1968 | Raymond et al. | ................. | 175/5 |
| 4,085,973 A * | 4/1978 | Payne | ................. | 299/8 |
| 4,234,046 A * | 11/1980 | Haynes | ................. | 175/6 |
| 4,345,461 A * | 8/1982 | Lezgintsev et al. | ........ | 73/170.32 |
| 4,538,683 A * | 9/1985 | Chulick | ................. | 166/264 |
| 4,709,584 A * | 12/1987 | Voll et al. | ................. | 73/864.44 |
| 4,838,079 A * | 6/1989 | Harris | ................. | 73/152.18 |
| 4,996,887 A * | 3/1991 | Voll et al. | ................. | 73/864.44 |
| 5,062,309 A * | 11/1991 | Voll et al. | ................. | 73/864.44 |
| 5,516,317 A * | 5/1996 | Moody | ................. | 441/2 |
| 7,392,856 B2 * | 7/2008 | Nance et al. | ................. | 175/20 |
| 7,757,573 B2 * | 7/2010 | Sauter | ................. | 73/864.65 |
| 8,191,436 B2 * | 6/2012 | Chun et al. | ................. | 73/864.44 |

FOREIGN PATENT DOCUMENTS

| | | |
|---|---|---|
| DE | 3635748 | 4/1988 |
| DE | 3930300 | 3/1991 |
| DE | 3931131 | 3/1991 |
| EE | 9800130 | 4/2000 |
| FI | 864147 | 4/1988 |
| SU | 1013810 | 4/1983 |
| SU | 1559261 | 4/1990 |
| SU | 1597663 | 10/1990 |

\* cited by examiner

*Primary Examiner* — Leonard Chang
*Assistant Examiner* — Natalie Huls
(74) *Attorney, Agent, or Firm* — Andrus, Sceales, Starke & Sawall, LLP

(57) ABSTRACT

Device for taking samples from the bottom boundary layer of a water body, consisting of compact bottom sediments, overlying water-saturated mud layer, and near-bottom water layer directly connected with the latter, belongs among oceanographic devices. Disturbance of the probes' structure is avoided by the construction of the device with several shorter tubes with their inlet holes being located at different heights, instead of one long sampling tube. There are distinctive tubes for taking samples from layers at different heights from the bottom. The sampling tube divided into sections is furnished with isolating valves that divide the interior of the tube into layers isolated from each other. Soft and regulated drop of the device is achieved using the inflatable contact belt. Using an upper inflatable balloon avoids the vertical stability of the device and raising it to the surface without cabling.

6 Claims, 4 Drawing Sheets

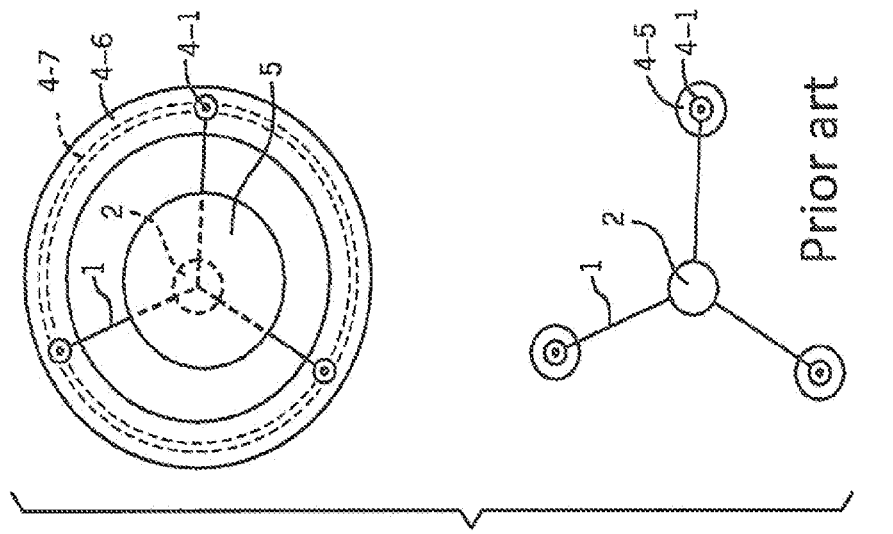
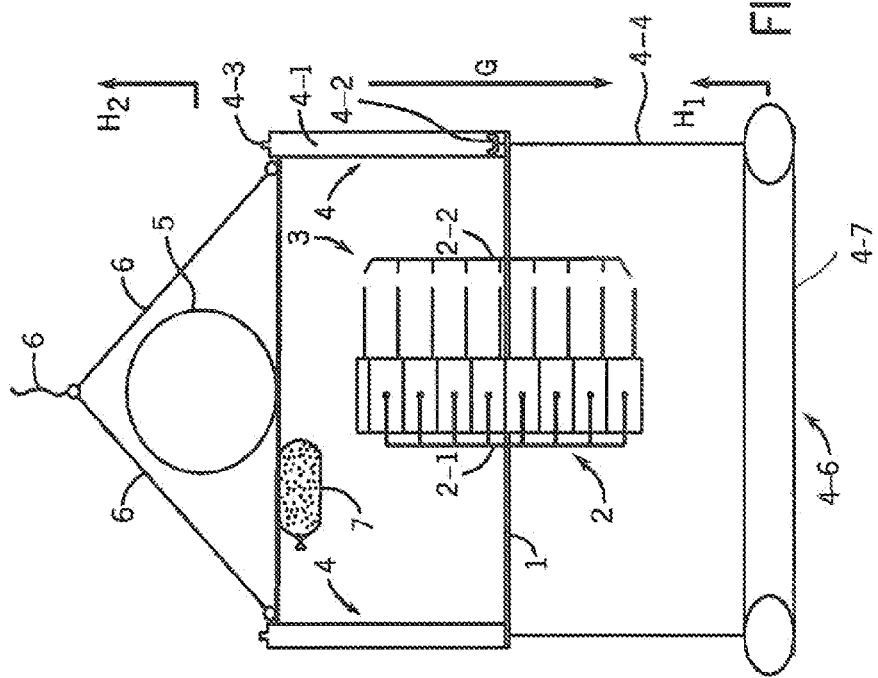
FIG. 3-1
FIG. 3-2

DEVICE FOR TAKING SAMPLES FROM THE BOTTOM BOUNDARY LAYER OF A WATER BODY

CROSS-REFERENCE TO RELATED APPLICATIONS

The present application claims priority from Estonian Patent Application No. P200900068, filed Sep. 9, 2009.

FIELD

The invention relates to the oceanographic instruments aimed at studying the structure and properties of elements in a water basin. More precisely, it belongs to the devices enabling to take non-mixed (undisturbed) samples from the boundary layer formed at the bottom of a water body. The boundary layer consists of compact bottom sediments, overlying suspended water-saturated mud layer, and near-bottom water layer directly connected with the latter.

BACKGROUND

The water body is characterized by the structure and concentration of elements in the boundary layer. The boundary layer formed at the bottom of a water body is labile in character (with an easily disturbable structure). It comprises much more substances and elements than can be found in the volume of the water body.

The instruments in use do not enable to sample the boundary layer in its original state in the bottom of a water body, because the penetration of the sampling tube into the sampling environment is accompanied by a smaller or greater shock. As a result, the boundary layer is crushed, pushed away from the sampling tube and does not get into it.

Still, it is possible to get samples from single macrocomponents (bottom vegetation, fauna, macroparticles of solid sediments).

To get a boundary layer sample with the least possible disturbance, an operable sampling device is needed, i.e. its movement and operations in the sampling environment should be adjustable.

Known is the device for taking samples from near-bottom water, water-saturated suspended mud and solid bottom sediments, the tube for sampling solid bottom deposits of which can be disassembled into separate sections (SU 1013810A1). To avoid the disturbance of bottom sediment structure on rapid penetration of the sampling tube into bottom sediments, the penetration speed is regulated by means of shock absorber unit (SU 1559261A1; U.S. Pat. No. 4,709,584; DE 3635748A1; FI 81413A). On taking near bottom water samples bathymeters are used, which are situated higher than the bottom sediment sampling tube and are in direct contact with the latter (U.S. Pat. No. 4,996,887; DE 3930300 A1). The closing mechanism of the lower opening of the sampling tube (SU 1597663A1; U.S. Pat. No. 5,062,309; DE 3931131 A1).

From the prior art is known a device for taking samples from the bottom boundary layer of a water body, which consists of the supporting frame with footings, the sampling tube disassemble into separate sections and the absorber units (EE9800130A).

Despite using the named above solutions, it is a drawback of such device when obtaining undisturbed samples that after a sample has been taken from the boundary layer the sectioning of the interior of the sampler's upper part (bathymeter) with valves helps to an extent avoid the mixing effect caused by oscillation and vibration due to waves and the flowing of the water (especially when the waves are high) when the device is lifted, but it has not been done in the lower part of the sampler that is foreseen for taking samples of solid bottom sediments and suspended mud.

Despite guidance, i.e. slow controlled lowering into the bottom layer of the body of water, sampler movement in the sampling environment may cause destruction of the initial structure of the sample, i.e. the mixing effect occurs due to friction (surface tension) between the inner wall of the sampling tube and the sampling environment. The degree of mixing depends on the distance of the sampling tube movement: the longer the way of sample movement in the sampling tube, the greater the mixing effect. Thus, the sample in the higher part of the sampling tube has been subject to a greater mixing effect than in the lower part. To obtain samples with the least possible disturbance, i.e. undisturbed samples, the sampling tube should have a minimal effect on the sampling medium.

In the water basins with a high organic matter inflow (shallow protected sea areas, eutrophied lakes, bog pools) a thick semiliquid suspended mud layer is formed. In the case of the known devices, the footings on the lower end of support rods of the shock absorber unit are not capable of retarding the descent of the device because their contact area is too small. The sampling tube penetrates at high speed into the sampling medium (near bottom water, suspended mud) and does not enable to get undisturbed samples from the boundary layer of a water body.

SUMMARY

In order to get samples of desired thickness in the form of isolated layers, the presented sampling tube is provided at its whole length with sectioning horizontal valves. These eliminate mixing of layers at the time the sampling tube is being lifted up and during the treatment onboard a vessel or in the lab.

To obtain undisturbed samples from the water column, boundary layer and bottom deposits with the least possible disturbance of the sediment structure by the sampling tube, the sampling tubes are provided with horizontal valves, which divide the tube into sections. The lower ends (intake apertures) of the tubes are located at different heights.

Preferably the sampling tubes are of different length.

Since the suspended mud has thicker consistency than free water, the motion of the descending device may be retarded on the upper boundary of suspended mud if the contact surface is sufficiently large to enable it and/or the weight of the device is small, i.e. pressure on the contact surface is low. For this purpose, the footings on the lower end of the shock absorber units have been replaced by support belt filled with gas. To effect the oval form, the supporting belt is made of elastic material, the cross-section area of which is adjustable by the amount of air or other gas used to fill the belt.

To guarantee vertical stability of the device, it is provided with a stabilizing balloon filled with gas at the top of the supporting frame. Preferably the stabilizing balloon has greater buoyancy than the supporting belt.

Appropriate dimensions and degree of filling of the stabilizing balloon and support belt are chosen so that the necessary smooth (floating-sinking) and guided descent onto the bottom of the body of water or the desired height from the bottom to take samples with the least possible disturbance is achieved.

By adjusting the degree of filling of the balloon and support belt with gas, one can change the buoyancy of the device, to facilitate descent to the bottom of the body of water and raising it to the surface without using a lifting cable.

Figures 1, 2:
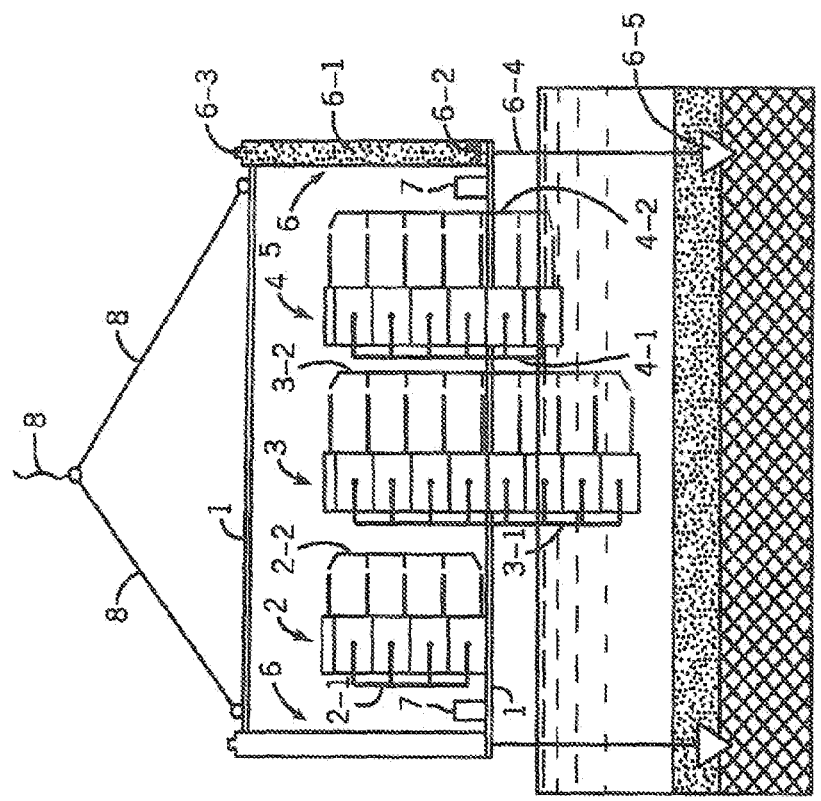
In FIG. 1-FIG. 3-3 the components comprised in the sampling device are marked with the following numbers and signs.
Figure 1:
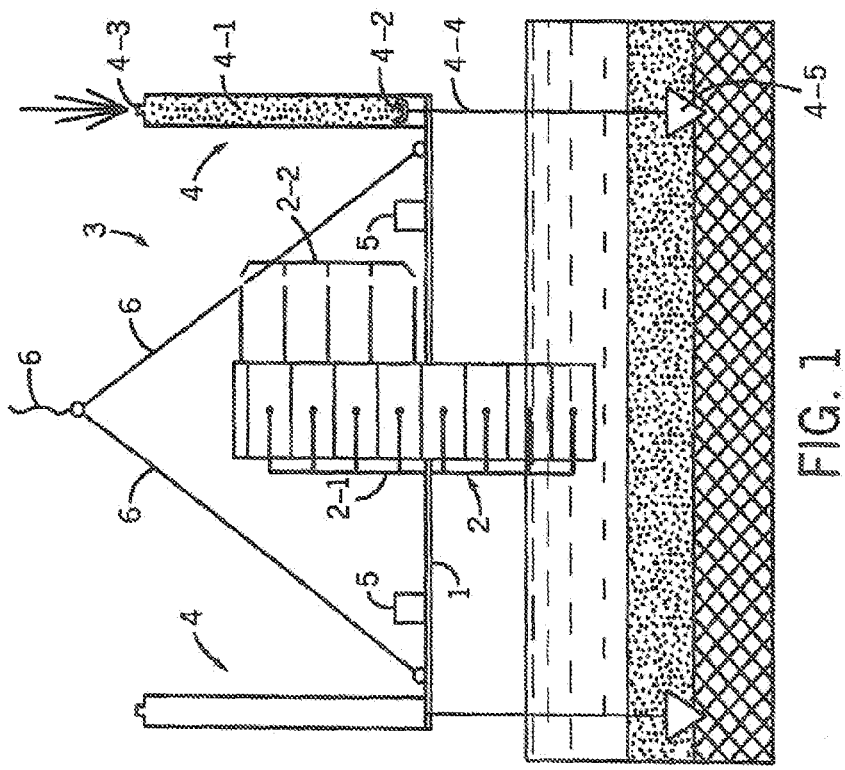
Figure 2:
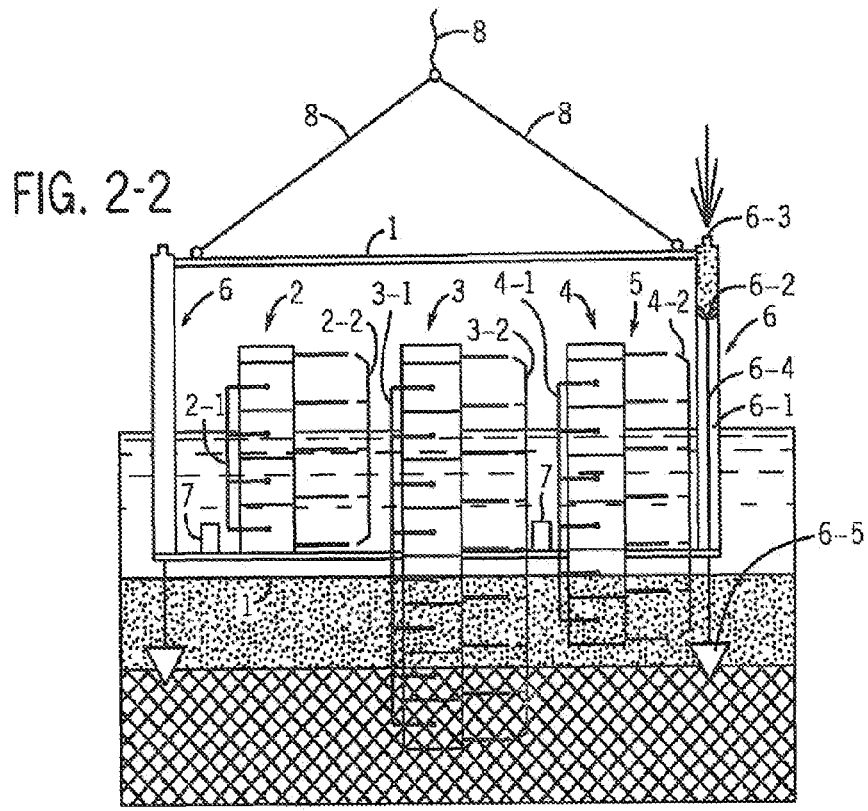
Figures 2, 3:
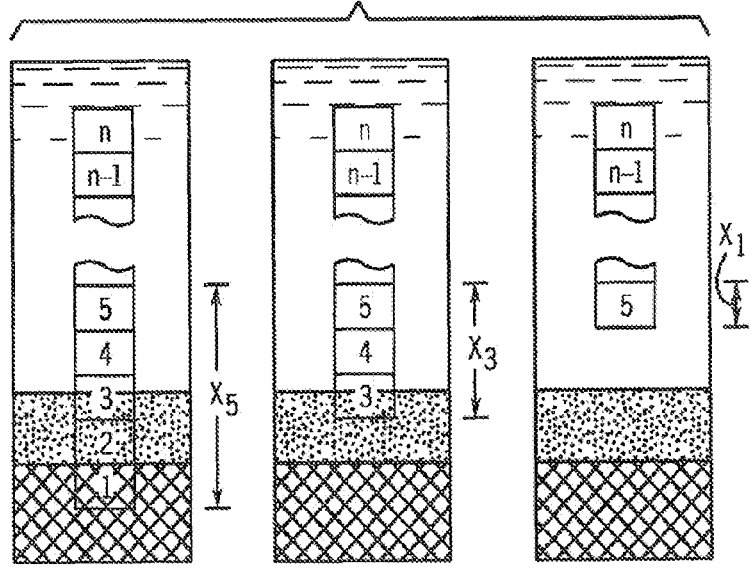
Figure 3:
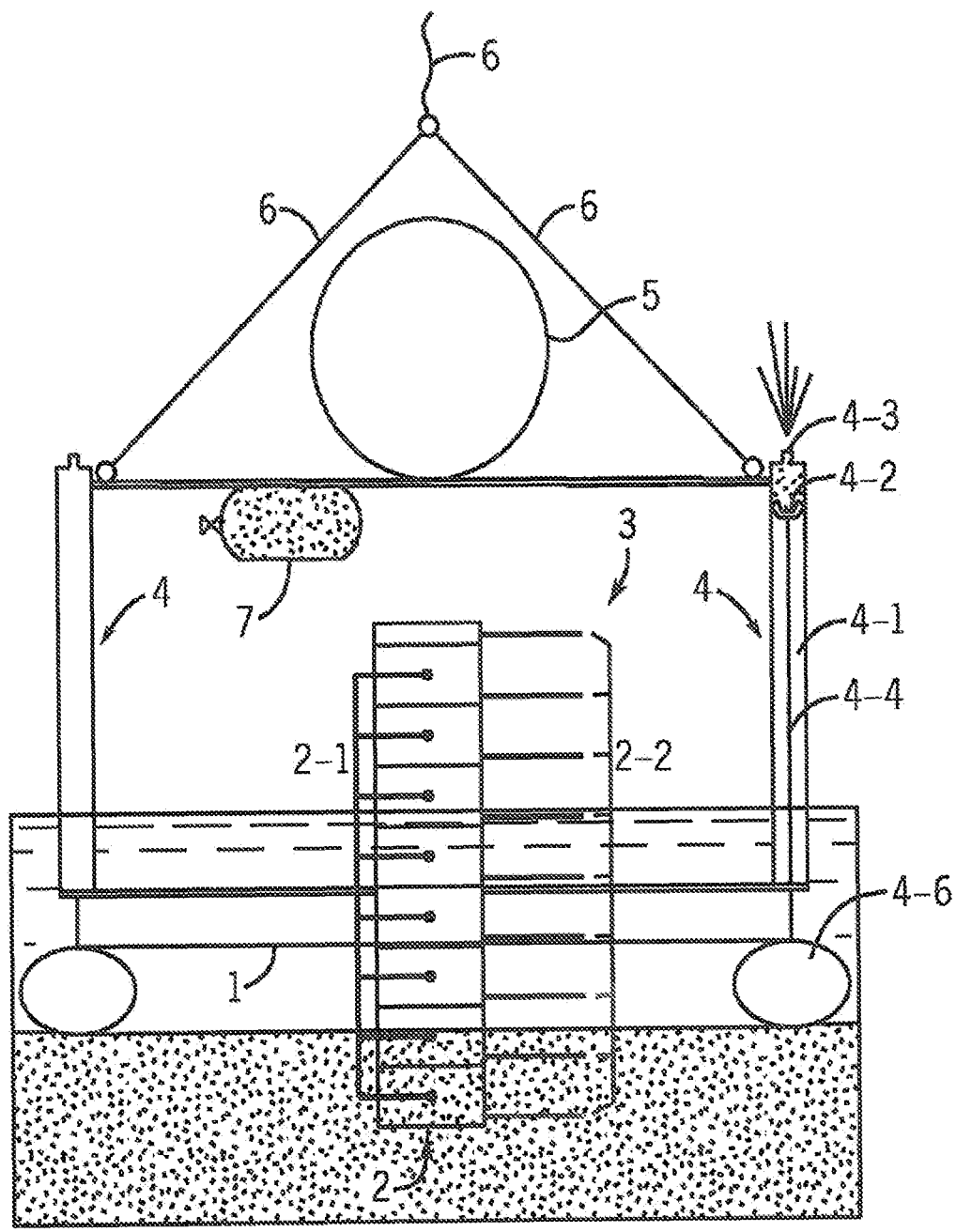

| Name of element | FIG. 1 | FIGS. 2-1 and 2-2 | FIG. 2-3 | FIGS. 1, 3-1, 3-2 and 3-3 |
|---|---|---|---|---|
| Supporting frame | 1 | 1 | | 1 |
| Sampling tube | 2 | 2,3,4 | | 2 |
| Section | 2-1 | 2-1, 3-1, 4-1 | | 2-1 |
| Horizontal valve | 2-2 | 2-2, 3-2, 4-2 | | 2-2 |
| Control unit | 3 | 5 | | 3 |
| Shock absorber unit | 4 | 6 | | 4 |
| Cylinder | 4-1 | 6-1 | | 4-1 |
| Hydraulic plunger | 4-2 | 6-2 | | 4-2 |
| Nozzle | 4-3 | 6-3 | | 4-3 |
| Support rod | 4-4 | 6-4 | | 4-4 |
| Footing | 4-5 | 6-5 | | 4-5 |
| Support belt | | | | 4-6 |
| Additional weight | 5 | 7 | | |
| Cable | 6 | 8 | | 6 |
| Stabilizing balloon | | | | 5 |
| High-pressure gas balloon | | | | 7 |
| Samples from the bottom to the top | | | 1, 2, 3, 4, 5, n-1, n | |
| The routs of sample (5-th) movement | | | $X_1, X_2$ and $X_3$ | |
| Weight of the device | | | G | |
| Buoyancy of the stabilizing balloon | | | $H_2$ | |
| Buoyancy of the support belt | | | $H_1$ | |

FIG. 1 presents the known device for sampling in water basins.

FIG. 2-1 shows the presented sampling device, which differs from the sampler presented in FIG. 1 in that, several sampling tubes located at different heights are used.

FIG. 2-2 depicts the final moment of sampling with the device presented in FIG. 2-1.

FIG. 2-3 shows the route of sample movement in the sampling tubes positioned at different heights.

FIG. 3-1 shows the presented sampling device, which differs from the known device in FIG. 1 in that, the footings 4-5 have been replaced with the support belt 4-6 and the stabilizing balloon to be filled with air or some other gas.

FIG. 3-2 is a view from above of devices depicted in FIGS. 3-1 and 1.

FIG. 3-3 shows sampling from the bottom of a muddy water basin by means of the presented device (FIG. 3-1).

DETAILED DESCRIPTION

FIG. 1 shows a known device coming in contact with the bottom of a water body. The sampling tube is lowered to the bottom by means of cables 6. Its movement slows down when the footings 4-5 of the shock absorber unit 4 come in contact with compact bottom sediments. At that time the upper edge of the sampling tube 2 has not yet touched the boundary layer, but remains above it.

FIG. 2-1 presents a sampling device for taking samples from the boundary layer on the bottom of a water basin, which differs from the device in FIG. 2-1 by the fact that not only one but several sampling tubes with their lower edges positioned at different heights are used. The sampling tubes consist of sections (2-1; 3-1; 4-1) and have isolating horizontal valves (2-2, 3-2, 4-2). The sampling device gets into contact with the bottom of a water body. The sampling tube is lowered to the bottom by means of cables 8. Its movement slows down when the contact elements 6-5 of shock absorbers touch compact bottom sediments. At that time the lower edge of the lowermost sampling tube 3 has not yet get any contact with the upper surface of the boundary layer, but remains higher.

FIG. 2-2 shows the penetration of the sampling tube into the boundary layer at a slow and regulated speed, its further movement in the sampling environment and sampling. The slow regulatable descent of the sampling tubes 2,3,4 depends on the functioning of shock absorbers 6. The device together with additional weight 7 exerts pressure on the hydraulic plungers 6-2 moving in the cylinders 6-1 of the shock absorber unit 6. The plunger starts moving upwards forcing the water out of nozzles 6-3 in the upper part of cylinders 6-1. The speed of descent depends on the dimensions of cylinders 6-1 and nozzles 6-3; the smaller the dimensions of nozzles 6-3 compared to cylinders 6-1, the slower the descent speed. The descent continues until the weight of the device equilibrates with the force of resistance to the movement of sampling tubes in the sampling medium.

FIG. 2-3 shows the route of 5-th sample movement in the sampling tubes positioned at different heights. $X_5$ corresponds to the lowest $X_3$ to an intermediate and $X_1$ to the upper tube. The higher is stay the lower end of the sampling tube the shorter is the route of sample movement.

FIG. 3-1 shows the presented device. It differs from the sampler in FIG. 1 in that the footings 4-5 on the lower end of support rods 4-4 of shock absorbers unit 4 have been replaced with support belt 4-6 made of elastic material, which can be filled with air or some other gas, or instead of footings a large contact surface is used. The upper stabilizing balloon 5 has been added. The support belt and stabilizing balloon are filled from the high-pressure gas balloon 7. To lower the device from the water surface to a certain depth a support belt with reduced cross section surface is used. The filling of the support belt with gas is started at a certain height from the bottom. With this, the buoyancy (=H1+H2+G) of the device is increased and the descent speed decreased. It is guaranteed that the motion of the device ceases when the support belt touches soft bottom sediments. Regulating the filling degree of inflatable balloon, it is possible to regulate the buoyancy of the sampler—make it stop at a certain height from the bottom of a water basin. After sampling, with further filling of the balloon with gas, the device can be lifted up to the surface at certain speed. No cables are used.

The forces influencing the sampling device are presented graphically. The resultant buoyancy $R=G+H_1+H_2$, where G is the weight of the device in water, $H_1$ and $H_2$ are the buoyancies of the support belt and the balloon, respectively. If $/H_1+H_2/>/G/$, the device rises to the surface without using any cable.

FIG. 3-2 Shows a view from above on the presented device depicted in FIG. 3-1 (upper drawing) and on the known device in FIG. 1 (lower drawing).

FIG. 3-3 shows sampling from the bottom of a muddy water basin by means of the presented in FIGS. 3-1 and 3-2 (upper drawing) device.

The invention claimed is:
1. A device for taking samples from the bottom boundary layer of a water body, the device comprising:
   a supporting frame;
   sectioned sampling tubes;

horizontal valves separating the sections of said sampling tubes;

shock absorber units;

support rods being part of said shock absorber units;

lower ends of said support rods;

lower intake apertures of said sectioned tubes near the bottom of the tubes;

inner walls of the sampling tubes;

wherein the lower intake apertures are located at different heights to take samples from different boundary layers minimizing the friction between the inner wall of the sampling tube and the sampling environment;

wherein to obtain undisturbed samples, each of the sectioned sampling tubes is provided with horizontal valves at its whole length, and wherein the lower ends of said support rods of said support frame are provided with a contact surface.

2. The device according to claim 1, wherein sectioned sampling tubes having different lengths are located at different heights from the bottom of the water body.

3. The device according to claim 1, wherein the contact surface is a support belt made of elastic material, the cross-section area of which is adjustable by the amount of air or other gas used to fill the belt.

4. The device according to claim 1, wherein to guarantee the vertical stability of the sampling device during sinking and lifting, the upper part of the supporting frame is provided with a stabilizing balloon filled with gas.

5. The device according to the claim 4, wherein the stabilizing balloon has greater buoyancy than the supporting belt.

6. The device according to claim 5, wherein the stabilizing balloon and the support belt are filled with gas providing a level of buoyancy that allows lowering the device onto the bottom of the body of water and raising it onto the surface without using lifting cables.

* * * * *